United States Patent [19]
Gaset et al.

[11] Patent Number: 4,590,283
[45] Date of Patent: May 20, 1986

[54] PROCESS FOR MANUFACTURING 5-HYDROXYMETHYLFURFURAL

[75] Inventors: Antoine Gaset; Luc Rigal, both of Toulouse; Gilles Paillassa, Pau; Jean-Paul Salomé, Vieux-Berquin; Guy Flèche, Merville, all of France

[73] Assignee: Roquette Freres, Lestrem, France

[21] Appl. No.: 650,637

[22] Filed: Sep. 14, 1984

[30] Foreign Application Priority Data

Sep. 14, 1983 [FR] France ............................... 83 14646

[51] Int. Cl.$^4$ ........................................... C07D 307/46
[52] U.S. Cl. .................................................. 549/488
[58] Field of Search ........................................ 549/488

[56] References Cited

U.S. PATENT DOCUMENTS 4,339,387  7/1982  Flèche et al. ...................... 549/488

FOREIGN PATENT DOCUMENTS 139473  10/1981  Japan .
2058070  9/1983  United Kingdom .

OTHER PUBLICATIONS

D. W. Brown, et al., "Dehydration Reactions of Fructose in Non-Aqueous Media", *Journal of Chemical Technology and Biotechnology*, vol. 32, No. 10, Oct., 1982, Oxford (Great Britain).
*Chemical Abstracts*, vol. 96, No. 11, Mar. 15, 1982, p. 576, Abstract No. 85408u, Columbus, Ohio (US).
*Chemical Abstracts*, vol. 96, No. 9, Mar. 1, 1982, p. 594, Abstract No. 68801z, Columbus, Ohio (US).
*Chemical Abstracts*, vol. 94, No. 19, May 11, 1981, p. 633, Abstract No. 156646s, Columbus, Ohio (US), Y. Nakamura: "Preparation of 5-(Hydroxymethyl)furfural by Selective Dehydration of D-Fructose", & Noguchu Kenkyusho Jijo, 1980, (23), 25–38.

*Primary Examiner*—Richard L. Raymond
*Attorney, Agent, or Firm*—Larson and Taylor

[57] ABSTRACT

The invention relates to a process for manufacturing 5-hydroxymethylfurfural consisting of bringing a hexose into contact with a catalytic support in the form of a solution of said hexose in a strongly polar aprotic solvent, particularly dimethylsulfoxide, the 5-hydroxymethylfurfural formed being extracted by means of a solvent for the latter also brought into contact with the catalytic support. All of the operations are carried out preferably continuously, particularly by the countercurrent principle.

6 Claims, 1 Drawing Figure

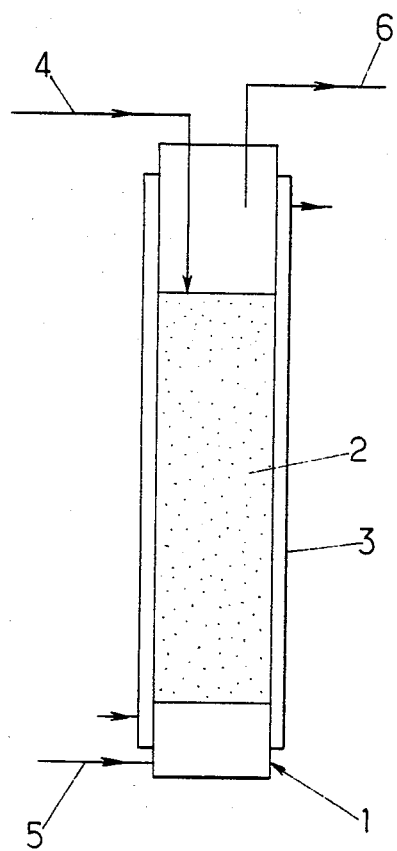

PROCESS FOR MANUFACTURING 5-HYDROXYMETHYLFURFURAL

BACKGROUND OF THE INVENTION

The invention relates to a process for manufacturing 5-hydroxymethylfurfural, denoted by HMF in the following, of the formula:

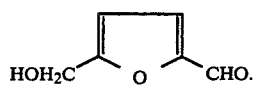

HMF is a conversion product of hexoses with 6 carbon atoms.

The conversion of the sugars is done in an acid medium and under the action of heat. It is characterized by a dehydration followed by cyclisation.

The hexoses comprise aldohexoses which have an aldehyde function and ketohexoses which have a ketone function.

Among aldohexoses, may be mentioned, for example, glucose, galactose, mannose, iodose and, among ketohexoses, fructose or levulose, sorbose, tagatose and allose.

More generally, any oligo- or polysaccharide whose transformation leads to aldohexoses and/or ketohexoses can be used as a starting material for the invention.

The mechanism of formation of HMF is represented generally by the diagram indicated below. Under the effect of acid on hexoses, intermediate products are formed whose structure is still very poorly understood and which give rise either to HMF, or to a group of compounds, called humins, which are insoluble polymerisation products. According to the operational conditions, the development of the intermediates will be oriented towards the formation of HMF or towards that of humins.

HMF can itself result in by-products either by opening of the ring (levulinic acid and formic acid), or by polymerisation thereby providing humins.

Reaction diagram:

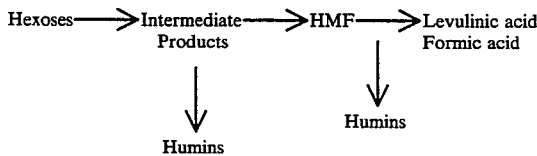

Applicants have already developed a process for manufacturing HMF by a conversion of hexoses, this process consisting of bringing the hexoses in aqueous solution in contact with an exchange resin with cationic function at a temperature below 100° C. and recovering the HMF formed by means of a solvent for the latter selected from among those whose water miscibility is as low as possible.

This process gives satisfaction, but in view of more and more severe economic requirements, Applicants have sought to improve it in the direction of an increased yield.

GENERAL DESCRIPTION OF THE INVENTION

This object has been achieved according to the invention by bringing the hexose into contact with a catalytic support in the form of a solution of said hexose in a strongly polar aprotic solvent selected from the group comprising dimethylsulfoxide or DMSO, dimethylformamide or DMS and N-methylpyrrolidone or NMP and by extracting the HMF formed by means of a solvent for the latter also brought into contact with the catalytic support, the operations of contacting the hexose solution with the catalytic support, on the one hand, and of extraction of the HMF formed, on the other hand, being carried out preferably continuously, particularly by the countercurrent principle.

In an advantageous embodiment of the above-said process, the catalytic support is placed inside a tubular reaction vessel, the supply of hexose in solution in the strongly polar aprotic solvent and the supply of extraction solvent being carried out at different points of the tubular vessel, preferably in the vicinities respectively of the upper and lower ends.

The invention also includes other features which are preferably used at the same time and which will emerge from the additional description and the examples which follow.

In order, consequently, to manufacture HMF in accordance with the invention, procedure is as follows or in equivalent manner.

The process according to the invention combines, in a heterogeneous catalysis carried out in the presence of a solid catalytic support and at a temperature below 100° C., the selection, on the one hand, of a strongly polar aprotic solvent in which is dissolved the sugar constituting the starting material and, on the other hand, an extraction solvent for the HMF formed as well as, preferably, recourse to continuous realization of the process (supplies and extractions) particularly according to the principle of counter-currents; the HMF being then extracted progressively with its formation is protected from the troublesome effects of temperature.

The sugar constituting the starting material is advantageously a hexose.

Preferably, ketose sugars such as fructose or levulose very widely found in nature, are utilized as well as any systems capable of giving rise to the formation of this sugar in the reaction medium or an appended device placed in series with the reaction vessel; for example, it would be possible to isomerise a dextrose solution and subject the dextrose-fructose mixture obtained to the conditions of the invention.

The hexose is solubilized in the strongly polar aprotic solvent or in a mixture of several of these solvents; the concentration of the solvent in sugar depends on the solubility of the sugar concerned. In the case of fructose and of DMSO, it is possible to employ solutions having concentrations of 100 to 500 g/l, preferably of 300 to 500 g/l.

It is in the aprotic solvent and in contact with the catalytic support that the dehydration reaction occurs and it is through the organic solvent of the HMF, which solvent is brought preferably in counter-current into contact with the catalytic support, that the HMF produced is extracted, progressively with its formation.

The catalytic support comprises cationic groups and is selected, preferably, from among strongly acid resins, containing preferably sulfonic groups; it is possible to mention, for example, those marketed under the trademarks "AMBERLIT C 200" (ROHM & HAAS) and "LEWATIT SPC 108" (BAYER).

The organic solvent used to extract the HMF formed is selected for its good aptitude to solubilize HMF, from among ketones and particularly methylisobutylketone, nitriles and particularly benzonitriles, ethers and particularly dimethoxyethane; it is also possible to use mixtures of these solvents. The reaction is carried out at temperatures comprises preferably between 70° and 80° C., and more preferably still between 75° and 80° C.

The amount of resin employed depends on its exchange power and is determined from the catalytic ratio R. Now, the exchange power is expressed in $H^+$ ion equivalents per gram of anhydrous support and the catalytic ratio is represented by the ratio R of the total exchange power to the number of moles of sugar employed per hour; the ratio R can be selected in the range running from 0.1 to 100 but, in practice, it is selected within the preferential range of 2 to 10 which leads to the best yields.

The process is advantageously employed in a tubular vessel shown overall at 1 in the single FIGURE and within which the catalytic support 2 is placed.

The temperature is kept in the catalytic support at the selected value, for example by resorting to a double jacket 3 with hot water circulation.

The strongly polar aprotic solvent in which the sugar to be transformed is dissolved is introduced through piping 4 into the vessel at a first point of the vessel, preferably situated in the vicinity of the upper end of the latter; the extraction solvent is introduced into the vessel through piping 5 at a point separate from that through which the sugar solvent is introduced, this point being situated preferably in the vicinity of the lower end of the vessel.

In this way extraction by the counter-current principle is effected.

The vessel is equipped with any suitable means to ensure optimum contact between the solid support and the solvents for introducing the sugar, on the one hand, and for extraction of the HMF formed, on the other hand; these means impart to the constituent grains of the resin a relative motion with respect to one another and can use the well-known principle of pulsed columns.

The extraction solvent for the HMF, having solubilized the latter and having entrained the aprotic solvent through which the sugar to be converted has been brought in, is recovered through piping 7 situated preferably in the vicinity of the upper end of the tubular vessel.

At the outlet of the vessel, the HMF formed from this mixture is recovered.

The supply flow rate of the installation in sugared solvent with respect to the volume V of moist resin employed and contained in the tubular vessel is selected so that the technicological characteristics of the installation are exploited to the best; for the concentrations indicated above of the DMSO in fructose, the flow rate selected is advantageously comprised between 0.03 V/hour and 0.3 V/hour.

Concerning the flow rate of the extraction solvent, it is quite evident that, the higher this flow rate, the more rapid is the recovery of the HMF formed; in spite of this fact, it is advantageous, for reasons of economy, to select flow rates of 0.5 to 15 V/hour, preferably comprised between 1 and 5 V/hour.

Finally as regards the ratio of the sugared solvent flow rate/extraction solvent, it has no great influence on the yield of the reaction; it is nonetheless selected so that after extraction of the HMF formed, the amounts of solvents to be distilled are as small as possible; in practice, it is selected between 2 and 300, preferably between 5 and 270 and, more preferably still, between 6 and 100.

In the examples which follow, there is used, as catalytic support, "LEWATIT SPC 108" resin and the contents of HMF are determined by gas chromatography after sililation of the HMF formed.

DESCRIPTION OF THE PREFERRED EMBODIMENTS

EXAMPLE 1

In a tubular reaction vessel 1 of 2 liters capacity of the above-described type, with an inner diameter of 60 mm, is introduced 1 liter of moist resin obtained from 225.5 g of dehydrated resin, moistened with DMSO.

The vessel is equipped with a double jacket for circulating water.

The temperature of the circulated water is 80° C. due to which the temperature existing within the vessel is kept at 76° C.

There is continuously added through the piping 4, by means of a pump arranged on this pipe, a fructose solution in dimethylsulfoxide at the concentration of 250 g of fructose per kg of DMSO, which corresponds to a density of 1.17. The addition is carried out at a constant flow rate of 213 cm$^3$/hour or 49.84 g of fructose/hour.

The total exchange power of the resin is 0.95 equivalent $H^+$ ion.

The catalytic ratio R is established at 3.43 since the number of moles of fructose per hour is 0.2767.

Through the piping 5, is introduced methylisobutylketone, called below MIBK, at a flow rate of 1500 cm$^3$/hour, as extraction solvent.

This extraction solvent traverses the tubular reactor in counter-current to the fructose solution in the DMSO; it is charged with HMF and with DMSO and is recovered at the head of the column.

After 100 hours of operation, the introduction of fructose is stopped and the resin is continued to be eluted for two hours with MIBK.

A total of 153 liters of solution is obtained containing:
3384.78 g of HMF (per 1 liter of moist resin contained in the vessel),
less than 0.2% by weight of levulinic acid
19.936 kg of DMSO,
and by-products, particularly humins.

From this solution, 3384.78 g of HMF is recovered.

The yield of the operation is represented by the formula:

$$100 \times \frac{\text{moles of HMF formed}}{\text{moles of fructose introduced}}$$

The number of moles of fructose introduced in 100 hours being 27.67, the number of moles of HMF formed 26.84, there is a yield of 97%.

By operating the installation under the same conditions for 200, then 300 hours, the same yield is always achieved.

By the expression "productivity" of the process, is meant the number of moles of HMF formed per hour and per $H^+$ equivalent.

In the case of the present example and taking into account the fact that 26.84 moles of HMF were formed in 100 hours and that the total exchange power of the resin is 0.95 $H^+$ equivalent, the value of the productivity is 0.282.

EXAMPLE 2

The same apparatus and the same operational conditions—except those specified below—as in Example 1 were used.

For 100 hours a 33.3% fructose solution in DMSO was introduced, that is to say a solution containing 500 g of fructose per kg of DMSO, which corresponds to a solution of a density of 1.25.

The hourly inflow rate was 56.3 ml of the solution concerned.

The exchange power of the resin being the same as in Example 1, the catalytic ratio is established at 7.294 since the number of moles of fructose introduced per hour is 0.1302.

Under these conditions, 1601.44 g of HMF were recovered per liter of moist resin contained in the vessel. The yield of the reaction is equal to 97.5% (number of moles of fructose introduced = 13.024 and number of moles of HMF formed = 12.688).

The productivity was 0.1335 moles of HMF/hour/H+.

EXAMPLE 3

The apparatus and the conditions of Example 1 were used, with the difference that the value of the extraction flow rate was lowered to 500 cm$^3$/hour.

The amount of HMF produced was then 3000.94 g per 1 liter of moist resin contained in the vessel.

The yield of HMF was 86% (number of moles of fructose introduced = 27.67, number of moles of HMF produced = 23.79).

Hence a reduction of 11% with respect to the value obtained in preceding Example 1 was recorded for an extraction flow rate of 1500 cm$^3$/hour.

The productivity was 0.250 moles of HMF/hour/H+, whereas it was 0.282 in Example 1.

EXAMPLE 4

This relates to a comparative example combining the results of 6 experiments carried out with the apparatus and under the conditions of Example 1 using successively, for the supply of hexose, various basic aprotic solvents.

The results obtained, that is to say the yield in percent of HMF, are reported in Table I.

TABLE I

| Solvent | DMSO | HMPT* | NMP | DMF | Acetonitrile | Pyridine |
|---|---|---|---|---|---|---|
| Yield in % HMF | 97 | 33 | 88 | 83.6 | 9.9 | 4.5 |

*HMPT: hexamethylphosphotriamide.

The results combined in Table I show that only the solvents provided according to the invention lead to high yields.

EXAMPLE 5

This relates to another comparative example combining 5 experiments, namely respectively:

two experiments (a) and (b) relating to the employment of the continuous counter-current process using water in place of the strongly polar aprotic solvent, two experiments (c) and (d) relating to the employment of the process according to the invention with the difference that there is no longer an extraction with the second solvent.

one experiment (e) relating to the use of the process discontinuously whilst however maintaining the polar aprotic solvent.

Experiment (a)

The apparatus and operational conditions of Examples 1 and 2 were used, except for the conditions specified below.

The supply of fructose was provided by means of an aqueous solution containing 54.6% by weight of fructose, its density being 1.25.

The supply flow rate was 36.6 cm$^3$/hour.

The total exchange power of the resin being unchanged, the catalytic ratio R was established at 7.14 since the number of moles of fructose introduced per hour was 0.133.

The extraction flow rate (MIBK) was 1500 cm$^3$/hour.

After 100 hours of operation, 604 g of HMF or 4.79 moles of HMF per 1 liter of moist resin contained in the vessel were recovered.

The number of moles of fructose introduced being 13.30, the yield was established at 36%.

The productivity was 0.0504 moles of HMF/hour/H+.

Experiment (b)

With respect to experiment (a), the extraction flow rate was increased to 14000 cm$^3$/hour.

In this way there was obtained, after 100 hours of operation, a solution containing 1258.3 g of HMF (or 9.98 moles) per 1 liter of moist resin contained in the vessel, which corresponds to a yield of 75%, the number of moles of fructose introduced being unchanged.

The productivity was 0.105 moles of HMF/hour/H+.

Experiment (c)

Whilst preserving the equipment and the conditions of Example 1, the extraction with the second solvent was eliminated and the HMF solution in DMSO was withdrawn at a flow rate equal to that of the supply (fructose solution in DMSO).

After 100 hours of operation, a solution containing 2564.8 g of HMF (20.34 moles) per 1 liter of moist resin contained in the vessel, was recovered.

Yield was 73.5%.

Productivity was 0.214 moles of HMF/hour/H+.

Experiment (d)

Under the conditions of Example 2, but eliminating, as in Experiment (c), extraction by a second solvent, there were collected after 100 hours of operation, a solution containing 1137.11 g of HMF (9.02 moles) per 1 liter of moist resin contained in the vessel; the yield was 69.3%.

The productivity was 0.0949 moles of HMF/hour/H+.

Experiment (e)

In a thermostated vessel of 5 liters capacity, was suspended in 2 liters of MIBK, a liter of moist cationic resin obtained from 225.5 g of dehydrated resin.

Into this suspension was introduced 342 g of a 33.3% fructose solution in DMSO, that is to say 0.632 moles of fructose.

The temperature was kept at 78° C. for 5 hours with stirring of the mixture.

The resin was then separated by filtration and washed with methylisobutylketone.

In this way 71.767 g of HMF (0.569 mole) was recovered per 1 liter of moist resin introduced into the vessel.

The exchange power of the resin being still the same and the number of moles of fructose 0.632, the catalytic ratio was established at 1.5.

The yield was 90% and the productivity 0.1198 moles of HMF/hour/$H^+$.

Comparison of the results recorded for the Examples 1 to 3 and the Experiment (a) to (e), which results are collected in Table II, shows clearly that only the combination of preferred features of the invention leads to the extremely favourable yields of 97% or more.

TABLE II

|  | Ex. 1 | Ex. 2 | Ex. 3 | Ex. 5 | | | | |
|---|---|---|---|---|---|---|---|---|
|  |  |  |  | Exp a | Exp b | Exp c | Exp d | Exp e* |
| Catalytic ratio R (Number of $H^+$ ions per mole of fructose) | 3.43 | 7.294 | 3.43 | 7.14 | 7.14 | 3.43 | 7.3 | 1.5 |
| Supply flow rate ($cm^3$/hour) | 213 | 56.3 | 213 | 35.1 | 35.1 | 213 | 56.3 | — |
| Extraction flow rate ($cm^3$/hour) | 1500 | 1500 | 500 | 1500 | 14000 | 0 | 0 | — |
| Concentration of fructose in % by weight in DMSO | 20 | 33.3 | 20 | 54.7 | 54.7 | 20 | 33.3 | 33.3 |
| Mass of HMF produced per liter of resin | 3384.80 | 1601.44 | 3000.94 | 604 | 1258.33 | 2564.8 | 1137.11 | 71.75 |
| Productivity (moles of HMF/hour/$H^+$) | 0.282 | 0.133 | 0.250 | 0.050 | 0.105 | 0.214 | 0.0949 | 0.1198 |
| Yield of HMF (%) | 97 | 97.5 | 86 | 36 | 75 | 73.5 | 69.3 | 90 |

*discontinuous operation

As a result of which and whatever the embodiment adopted, there is thus provided a process for synthesis of HMF, of high performance and having, with respect to those which were already known, numerous determinative advantages among which especially:

the fact that it practically does not give rise to side reactions and decomposition products, the fact that it provides high yields, the fact that it permits an extremely long life of the catalyst.

We claim:

1. Process for manufacturing 5-hydroxymethylfurfural from a hexose by heterogenous catalysis in contact with a solid catalytic support comprising a strongly acid resin and at a temperature between 70°–80° C., comprising bringing the hexose into contact with the catalytic support said hexose being in the form of a solution of said hexose in a strongly polar aprotic solvent selected from the group consisting of dimethylsulfoxide (DMSO), dimethylformamide (DMF) and N-methylpyrrolidone (NMP), extracting the 5-hydroxymethylfurfural formed by means of a solvent therefor selected from the group consisting of ketones, nitriles and ethers, said solvent being also brought into contact with the catalytic support, the operations of contacting the hexose solution with the catalytic support, on the one hand, and of extraction of the 5-hydroxymethylfurfural formed, on the other hand, being carried out continuously, by the counter-current principle, a volume V of moist catalytic support being placed inside a reaction vessel, corresponding to an amount such that the catalytic ratio is 0.1 to 100, the supply of hexose in solution in the strongly polar aprotic solvent and the supply of extraction solvent being effected in the vicinity respectively of the upper and lower ends of the reaction vessel, the feed flow rate of the hexose containing solvent fed with respect to the volume V of moist catalytic support being 0.03 to 0.3 V/hour, and the flow rate of extraction solvent with respect to the volume V of moist catalytic support being 0.5 to 15 V/hour.

2. Process according to claim 1, wherein the heterogeneous catalysis is carried out at a temperature between 75° to 80° C.

3. Process according to claim 1, wherein the hexose containing solvent comprises a solution of 100 to 500 g of fructose per liter in DMSO.

4. Process according to claim 1, wherein the flow rate of extraction solvent with respect to the volume V of moist catalytic support is 1 to 5 V/hour.

5. Process according to claim 1, wherein the catalytic support comprises strongly acid cationic exchange resin containing sulfonic groups.

6. Process according to claim 1, wherein the solvent extracting the 5-hydroxymethylfurfural is selected from the group consisting of methylisobutylketone, bezonitriles, and dimethoxyethane.

* * * * *